US008080692B2

(12) United States Patent
D'Hondt et al.

(10) Patent No.: US 8,080,692 B2
(45) Date of Patent: Dec. 20, 2011

(54) CATALYTIC PROCESS FOR THE PRODUCTION OF OXYGENATED HYDROCARBONS

(75) Inventors: Els D'Hondt, Antwerp (BE); Pierre Jacobs, Gooik (BE); Bert Sels, Balen (BE)

(73) Assignee: Katholieke Universiteit Leuven (BE)

( * ) Notice: Subject to any disclaimer, the term of this patent is extended or adjusted under 35 U.S.C. 154(b) by 255 days.

(21) Appl. No.: 12/520,941

(22) PCT Filed: Dec. 27, 2007

(86) PCT No.: PCT/BE2007/000132
§ 371 (c)(1),
(2), (4) Date: Jun. 23, 2009

(87) PCT Pub. No.: WO2008/077205
PCT Pub. Date: Jul. 3, 2008

(65) Prior Publication Data
US 2010/0022807 A1    Jan. 28, 2010

(30) Foreign Application Priority Data
Dec. 27, 2006 (GB) .................................. 0625614.3

(51) Int. Cl.
*C07C 31/18* (2006.01)
*C07C 29/132* (2006.01)
(52) U.S. Cl. ........ 568/861; 568/449; 568/486; 568/862; 568/863

(58) Field of Classification Search .................. 568/861, 568/862, 863, 449, 486
See application file for complete search history.

(56) References Cited

U.S. PATENT DOCUMENTS

| 5,214,219 A | 5/1993 | Casale et al. |
| 6,080,898 A | 6/2000 | Drent et al. |

FOREIGN PATENT DOCUMENTS

| EP | 0 523 015 | 1/1993 |
| WO | WO 99/05085 | 2/1999 |
| WO | WO 2005/095536 | 10/2005 |

OTHER PUBLICATIONS

International Search Report and Written Opinion (PCT/BE2007/000132) mailed Feb. 5, 2008.
International Preliminary Report on Patentability (PCT/BE2007/000132) mailed May 2, 2009.
Official Communication from the European Patent Office for European Patent Application No. 07 855 379.9, dated Apr. 8, 2011.
Communication from European Patent Office regarding EP 07 855 379.9-2103, dated Jul. 26, 2011.

*Primary Examiner* — Elvis O Price
(74) *Attorney, Agent, or Firm* — Clark & Elbing LLP

(57) ABSTRACT

The invention relates generally to the production of oxygenated hydrocarbons such as lower alcohols and more preferably 1,2-propanediol. More particularly, this invention comprises a single-step catalytic process for the catalytic production of lower alcohols such as methanol, ethanol, ethylene glycol and 1,2-propanediol from glycerol in aqueous medium. The catalyst comprises a metal selected from the Group VIII transition metals, preferably platinum, alloys thereof and mixtures thereof and a microporous carrier, preferably a faujasite-type zeolite.

21 Claims, No Drawings

CATALYTIC PROCESS FOR THE PRODUCTION OF OXYGENATED HYDROCARBONS

CROSS-REFERENCE TO RELATED APPLICATIONS

This application is the national stage of International Application No. PCT/BE2007/000132, filed Dec. 27, 2007, which claims benefit of British Application No. GB 0625614.3, filed Dec. 27, 2006.

BACKGROUND OF THE INVENTION

A. Field of the Invention

The invention relates generally to the production of oxygenated hydrocarbons such as lower alcohols and preferably 1,2-propanediol. More particularly, this invention comprises a single-step catalytic process for the catalytic production of lower alcohols such as methanol, ethanol, propanol, ethylene glycol and 1,2-propanediol from glycerol. This invention relates to valorizing glycerol, which is a byproduct from saponification and transesterification processes, e.g. for the production of biodiesel, into value-added chemicals. The catalyst comprises a metal selected from the Group VIII transition metals, preferably platinum, alloys thereof and mixtures thereof deposited on a porous carrier, preferably a microporous carrier, and more preferably a faujasite Y-type zeolite.

Several documents are cited throughout the text of this specification. Each of the documents herein (including any manufacturer's specifications, instructions etc.) are hereby incorporated by reference; however, there is no admission that any document cited is indeed prior art of the present invention.

B. Description of the Related Art

Previous disclosures in the art for the one-pot conversion of glycerol to 1,2-propanediol describe the use both homogeneous and heterogeneous catalytic systems The application of pressures of a second reagent such as $H_2$.

Patent WO9905085 by Wabe et al. describes the reaction of 10 wt % glycerol with a homogeneous catalyst composed of an organic Pd-complex in the presence of sulpholane and water at 140° C. and a pressure of 5.2 MPa synthesis gas (syngas ($H_2$/CO)) for 19 h. The conversion of glycerol in a continuous reactor is 13 mol/mol.h with a 1,2-propanediol selectivity of 22%. These inventors also tested Pd and Ru catalyst on carbon and a Rh-complex.

U.S. Pat. No. 4,642,394 by Che et al. describes the reaction of 30 wt % glycerol in presence of a homogeneous catalyst, Rh(CO)$_2$acac with $H_2WO_4$, in 1-methyl-2-pyrrolidinone as a solvent. The reaction is carried out at a temperature of 200° C. with a pressure of 31.7 MPa syngas .($H_2$/CO) for 24 h. The reaction yielded 19% 1,2-propanediol and 18% 1,3-propanediol at a conversion of 39% and selectivities of 49 and 45%, respectively. In this document the testing of catalysts composed of Fe, Co, Ni, Ru, Pd, Os or Pt and other aprotic organic solvents, was also described.

Gallezot et al. published in Green Chemistry 6 (2004) the reaction for 168 h of 20 wt % aqueous solution of glycerol with 8 MPa of $H_2$ and CuO/ZnO as a heterogeneous catalyst at a temperature of 180° C. At a conversion of 19% they obtain a selectivity for 1,2-propanediol of 100%. Pd/C, Rh/Al$_2$O$_3$, Rh/Nafion, Rh/HY as catalysts, water, sulpholane and dioxane as solvents and Fe-, Ni-, Mn-, Cu-salts and HCl as additives, were claimed as well.

In Catalysis Communications 6, 645-649 (2005) Kusunoki et al. describe the reaction for 40 h of 20 wt % aqueous solution of glycerol with 4 MPa of $H_2$ and Ru/C with Amberlyst 15 as a heterogeneous catalyst at a temperature of 120° C. At a conversion of 33% a 1,2-propanediol selectivity of 60% was obtained, yielding 20% of 1,2-propanediol. Pt/C, Pd/C, Rh/C with homogeneous or heterogeneous acids ($SO_4^{2-}$/$ZrO_2$, BEA, USY, MFI, $H_2WO_4$) were also claimed as catalysts.

Dasari et al., Applied Catalysis A: General 281, 225 (2005), obtained high yields of 1,2-propanediol after 24 h in moderate conditions with CuCr as an heterogeneous catalyst at a temperature of 200° C. and a pressure of 1.4 MPa of $H_2$. At a conversion of 69% a selectivity for 1,2-propanediol of 72% was obtained. Ru/C, Ru/alumina, Pd/C, Pt/C, Raney nickel, Raney copper, Cu, Ni/C and Ni/silica-alumina were also used as heterogeneous catalysts.

In WO 2005/095536 A2, the conversion of glycerol to 1,2-propanediol with high selectivity is described. The reaction proceeds at 200° C. for 24 h in a closed reactor, pressurized with 1.4 MPa of $H_2$. A prereduced commercial copper chromium converts 86% of a 57 wt % crude glycerol feedstock to 1,2-propanediol with a selectivity of 80%.

In EU Patent 1 440 046 (2004), 25 wt % glycerol in water is converted within 4 h at a temperature of 230° C. under a $H_2$-pressure of 12.4 MPa, using a ReNi multimetallic heterogeneous catalyst with NaOH as a homogeneous additive, to yield 54% of 1,2-propanediol with a conversion of 61% and a selectivity of 88%.

Schuster et al. describe in U.S. Pat. No. 5,616,817 (1997) the full conversion of glycerol to yield 96% of 1,2-propanediol in severe process conditions. The heterogeneous catalyst comprises a mixed oxide of Co, Cu, Mn and Mo and $H_3PO_4$ as homogeneous additive. The reactions are carried out for 6 h at 230° C. and a hydrogen pressure of 25 MPa.

In U.S. Pat. No. 5,276,181 (1994), Casale et al. obtain 1,2-propanediol yields of 75% in severe process conditions. All glycerol form a 30 wt % aqueous solution is converted at 240° C. for 2 h under 13 MPa of hydrogen, using RuS/C as a heterogeneous catalyst and addition of NaOH.

Casale et al., U.S. Pat. No. 5,214,219, 1993), were using CuZn-oxide/Al$_2$O$_3$ as a heterogeneous catalyst. After 2 h at 270° C. and with a hydrogen pressure of 10 MPa, a 30 wt % aqueous glycerol solution is almost fully converted, with a 1,2-propanediol selectivity of 84%.

Montassier et al. (Journal of Molecular Catalysis, 70 (1), 99 (1991)) reported the conversion of diluted aqueous glycerol into 1,2-propanediol at 210° C. and a hydrogen pressure of 6 MPa, with a heterogeneous Ru/C. At full conversion, a yield of 75% of 1,2-propanediol was obtained.

Montassier et al., also reported (Heterogeneous Catalysis and Fine Chemicals, Studies in Surface Science and Catalysis, 41, 165 (1988)) a method for producing 1,2-propanediol from a 1 to 4 wt % aqueous solutions of glycerol. Raney Cu was used as heterogeneous catalyst in a reaction at 240° C. for 6 and a hydrogen pressure of 3 MPa 1,2-Propanediol yields of 57% were obtained with conversions of 86% and selectivities of 66%). Cu, Co, Pt, Ru, Rh and Ir/silica, Raney Co and Raney Ni catalysts were claimed as well.

SUMMARY OF THE INVENTION

In accordance with the purpose of the invention, as embodied and broadly described herein, the invention is broadly drawn to a single step process for the production of lower alcohols, such as methanol, ethanol, 1,2-propanediol, etc from glycerol, by contacting glycerol with a catalyst consisting of (i) a supported metal selected from the Group VIII metals, alloys thereof and mixtures thereof, and a porous, preferably a microporous material, and more preferably (ii) a faujasite Y-type zeolite as a second catalyst component or a the catalyst carrier.

In one aspect, the process converts glycerol, such as obtainable from the transesterification process, into lower alcohols such as methanol and ethanol, which can be reused in the transesterification process.

In a specific aspect, the invention concerns a single step process for the production of 1,2-propanediol from glycerol by contacting the substrate with a catalyst consisting of (i) a supported metal selected from the Group VIII metals, alloys thereof and mixtures thereof, and a porous, preferably a microporous material, and more preferably (ii) a faujasite-type zeolite as the catalyst carrier.

The supported metal can be prepared by ion exchange or impregnation and preferably impregnation. By impregnation is meant the broad definition that is usually used by experts in the field including impregnation methods like dry and incipient wetness impregnation. An impregnation procedure for instance comprises the introduction of a metal precursor such as a metal salts aqueous solution in the pores of the catalyst carrier, without necessarily filling the pore volume of the catalyst completely. The amount of water used for impregnation is determined as a weight percentage of the carrier in contact with ambient air. Typically, for the incipient wetness impregnation, 1.25 g of an aqueous metal salt solution or 94 wt % is added to 1.33 g of NaY zeolite. The weight percentage of the aqueous metal salt solution preferably is from about 0.01 to about 94 wt % and more preferably from 15 to 94 wt %.

In another aspect of the invention the supported metal is prepared by using an ammine complex salt which is then decomposed. Furthermore the supported metal is selected from the Group VIII transition metals, more specifically platinum, alloys thereof and mixtures thereof. The metals for alloys or mixtures of platinum may be Pd, Rh, Ru, Cu, Cr, Sn or Ni and the carrier can be loaded with metal up to 6 wt % and more preferably between 0.05 to 4 wt %.

Another aspect of the invention relates to a single-step process for the production of lower alcohols such as 1,2-propanediol from glycerol, which is carried out using a metal of Group VIII transition metals, supported on alkali containing zeolites. The FAU topology is preferred. A zeolite Y partially or fully exchanged with Na, K, Rb or Cs, or mixtures thereof, is preferably used. NaY-type zeolites with atomic Si/Al ratios between 2 and 10 are the most preferred catalyst carriers.

In another aspect of the invention, the final catalyst consists of a mixture of two components, viz. the zeolite with FAU topology and a traditional metal-on-support catalyst, such as Pt-on-carbon. The ratio of both compounds in the mixture is such that the metal and FAU zeolite in the reactor obey the preferred ratios defined above for single component mixtures.

In a particular aspect of the invention, the single-step process for the production of lower alcohols such as 1,2-propanediol uses a glycerol-containing feedstock with a concentration range of 1 to 100 wt % glycerol in water, preferably a concentration between 5 and 50 wt %, and most preferably between 10 and 40 wt %.

The process of the present invention converts glycerol to lower alcohols such as methanol, ethanol, propanol, ethylene glycol, 1,2-propanediol etc, with a combined selectivity for lower alcohols of about 70%, and a selectivity for 1,2-propanediol of about 50%, at glycerol conversion of about 90% or higher.

Further characteristics of the present invention relate to the temperature of the reaction. The temperature used in the reaction preferably ranges from 180 to about 300° C., and more preferably from about 200 to 260° C.

In still another aspect of the invention, the glycerol conversion runs in absence of added hydrogen and is carried out under atmospheric pressure of air or of an inert gas like nitrogen or helium.

In yet another aspect of the invention the main lower alcohols obtainable are ethanol, n-propanol, methanol, 1,2-propanediol and ethylene glycol.

Further scope of applicability of the present invention will become apparent from the detailed description given hereinafter. However, it should be understood that the detailed description and specific examples, while indicating preferred embodiments of the invention, are given by
way of illustration only, since various changes and modifications within the spirit and scope of the invention will become apparent to those skilled in the art from this detailed description. It is to be understood that both the foregoing general description and the following detailed description are exemplary and explanatory only and are not restrictive for the invention, as claimed.

The present invention concerns catalytic process for the production of lower alcohols from glycerol, characterised in that the process of glycerol conversion is a single-step catalytic process which is independent of addition of nitrogen gas or does not require addition of hydrogen comprising subjecting a water and glycerol reaction mixture to heating in the presence of an heterogeneous catalyst comprising a metal on a microporous carrier and to set reaction mixture in amounts sufficient to induce or to control catalytic hydrogenation. Such heterogeneous catalyst can comprise an acid microporous carrier. In this process glycerol can be converted with the reaction mixture under an inert atmosphere or with the reaction mixture under air. The process of glycerol conversion can be carried out with the reaction mixture under atmospheric pressure of air or of an inert gas like nitrogen or helium or even with the watery solution of glycerol being subjected to vacuum. Eventually the reaction mixture is subjected to a gaseous mixture that contains less than 20 parts per million, preferable less than 2 parts per million of hydrogen or to a gaseous mixture that contains less than 0.8 parts per million of hydrogen or to a gaseous mixture which is hydrogen free. A required carrier for the catalyst is a microporous carrier such as zeolite and preferably an acid zeolite and most preferably a faujasite-type zeolite carrier. By the process of present invention the glycerol is converted in a lower alcohol such as ethanol, methanol 1,2-propanediol or a mixture thereof. The catalyst used in this process is (i) a heterogeneous catalyst from the group consisting of metals selected from the Group VIII metals, alloys thereof and mixtures thereof, and (ii) a microporous carrier such as an acid zeolite carrier. The catalyst used in the process of present invention can be catalyst with (i) a heterogeneous catalyst from the group consisting of supported metals selected from the Group VIII metals, alloys thereof and mixtures thereof, and (ii) a faujasite-type zeolite or it can be a catalyst with (i) a heterogeneous catalyst from the group consisting of metals selected from the Group VIII metals, alloys thereof and mixtures thereof on a carbon support, and (ii) a faujasite-type zeolite. Such supported metal can be prepared by ion exchange or impregnation, and preferably by impregnation. In a particular embodiment of present invention the amount of aqueous salt solution used for impregnation is from 0.01 to about 94 wt % of the catalyst support, more preferably from 15 to about 94 wt %. In the catalytic process as described above the initial concentration of glycerol is from 1 to 100 wt %, preferably from 5 to 50 wt % and most preferably from 10 to 40 wt. Moreover the supported metal can be prepared by using an amine complex salt which is then decomposed. Such supported metal can be selected from the Group VIII transition metals, alloys thereof and mixtures thereof. Metals for alloys or mixtures of platinum may be Pd, Rh, Ru, Cu, Cr, Sn or Ni and the carrier is loaded with metal up to 6 wt % and more preferably between 0.05 to 4 wt %. The supported metal is preferably platinum or alloys thereof and mixtures thereof and such alloys or mixtures of platinum may comprise a metal of the groups consisting of Pd, Rh, Ru, Cu, Cr, Sn and Ni. In a particular embodiment the catalytic process for the catalytic process of present invention the carrier is loaded with metal up to 6 wt % and preferably the carrier is loaded with metal between 0.05 to 4 wt %. In a certain embodiment of present invention the zeolite support is an alkali form of Y-zeolite like NaY, KY, RbY and CsY, and more preferably NaY with 2<Si/Al<5. In yet another embodiment of present invention the catalytic process has a glycerol conversion of about 90% or higher is obtained, with a combined selectivity of lower alcohols of about 70%, also a glycerol conversion of 90% or higher can be obtained, with a combined selectivity of lower alcohols of 70% or higher or even a glycerol conversion of about 90% or higher can be obtained, a combined selectivity of lower alcohols of about 70% of which at least 50 mol % is 1,2-propanediol or a glycerol conversion of 90% or higher can be obtained, a combined selectivity of lower alcohols of 70% or higher of which at least 50 mol % is 1,2-propanediol.

A preferred reaction temperature for the catalytic process of present invention is the temperature is from 180 to 300° C. and more preferably from about 200 to 250° C. For such process the reaction pressure can be atmospheric.

Furthermore the present invention concerns the use of an acid heterogeneous catalyst comprising a molecular sieve and a metal selected from the Group VIII metals, alloys thereof and mixtures thereof in a single-step catalytic process with addition of a gas that contains less than 20 parts per million, preferable less than 2 parts per million of hydrogen or most preferably less than 0.8 parts per million of hydrogen or without addition of any hydrogen for the selective production of lower alcohols from glycerol. The above mentioned materials can be used in such process of present invention.

DETAILED DESCRIPTION OF EMBODIMENTS OF THE INVENTION

The term "single-step process" refers to a sequence of chemical transformations occurring in a single reactor.

The term "microporous carrier" as used herein refers to a solid with pores the size of molecules. It includes but is not limited to microporous materials, ALPOs and (synthetic) zeolites, pillared or non-pillared clays, carbon molecular sieves, microporous titanosilicates such as ETS-10, microporous oxides. Microporous carriers can have multimodal pore size distribution, also referred to as ordered ultramicropores (typically less than 0.7 nm) and supermicropores (typically in the range of about 0.7-2 nm). A particular type of microporous carriers envisaged within the present invention, are the molecular sieves and molecular sieve zeolites, more particularly the crystalline microporous carriers with faujasite topology, silica zeogrids and/or zeolites.

In the nomenclature of the molecular sieves or microporous carriers the pore size of <20 Å is considered microporous and 20-500 Å is considered mesoporous.

The pore size of molecular sieves can further be influenced by the nature of the templating molecules in the synthesis. The addition of swelling agents to the synthesis mixture can further affect the pore size of the resulting molecular sieve. Zeolites with different pore size have been well characterized and described by Martin David Foster in "Computational Studies of the Topologies and Properties of Zeolites", The Royal Institution of Great Britain, Department of Chemistry, University College London, a thesis submitted for the degree of Doctor of Philosophy, London, January 2003.

Although various catalytic processes for the single-step conversion of glycerol to lower alcohols such as 1,2-propanediol have been developed, none of them show the advantages of in this invention. The present single-step process under surprisingly mild pressure and temperature conditions requires no prior catalyst activation, no use of homogeneous additives and no applied pressures of a second reagent such as $H_2$. At the mild conditions, high yields of lower alcohols including for example methanol, ethanol, n-propanol, ethylene glycol and 1,2-propanediol can be obtained.

An object of this invention is the production of 1,2-propanediol from an aqueous solution of glycerol, such as is obtainable from transesterification processes of fats and oils, under very mild conditions with bio-ethanol, bio-methanol, bio-ethylene glycol as co-products.

According to the present invention, there is provided a single-step process for the production of oxygenated hydrocarbons, preferably 1,2-propanediol, from glycerol. The method comprises the selective deoxygenation of glycerol in presence of a metal containing catalyst.

The catalyst comprises a metal selected from the Group VIII transition metals, preferably platinum, alloys thereof and mixtures thereof deposited on a carrier. The carrier may be microporous, and is preferably a zeolite with FAU topology. Microporous carriers with a FAU structure type code that are suitable for the present invention, are defined in the databases of the International Zeolite Association (IZA) (htto://topaz.ethz.ch/IZA-SC/StdAtlas.htm). The materials with FAU type structure encompass type materials such as NaY zeolite, and related materials with isotypic framework structure. The whole family of materials belonging to the faujasite family that can serve as microporous catalyst carrier, can be found in the catalog of databases of the Structure Commission of the International Zeolite Association (http://www.iza-structure-.org/databases/catalog/Faujasite.pdf).

In the present invention preferably a faujasite-type zeolite such as NaY zeolite with Si/Al framework composition between 2.1 and 10.0, is used as a carrier for the metal. Related zeolite material such as mixed phases or FAU zeolites with increasing Si/Al content, such as described in a German patent, DE 2 324 235 (1974), may be used as carrier as well.

A further object of this invention relates to the service time and stability of the catalyst. The catalysts described here keep their activity during subsequent runs.

In contrast to the prior art, the present invention relates to a single-step process under very mild conditions using water as solvent, but not requiring homogeneous additives such as acid or base compounds.

In the known art, Japanese patent 6 211 724 and U.S. Pat. No. 5,426,249, describe multi-step processes contacting the subsequent substrates in different reactors, while this invention only uses one single reactor.

In contrast to the prior art, the present invention relates to a single-step process under very mild conditions using water as solvent, but not requiring the addition of hydrogen. Existing single-step processes, such as described in EU patent 1 440 046, U.S. Pat. No. 5,616,817, U.S. Pat. No. 5,276,181 and U.S. Pat. No. 5,214,219, require high hydrogen pressures in order to obtain high 1,2-propanediol yields. Montassier et al. (Journal of Molecular Catalysis, 70 (1), 99, 1991) also describe an application using high hydrogen pressures, of at least 3 MPa. Whereas some examples, like Dasari et al. (Applied Catalysis A: General, 281, 225, 2005 and Suppes et al. WO 2005/095536 A2) operate under milder conditions, for example 200° C. and 1.4 MPa of $H_2$, no catalytic system is described that allows the production of high yields of lower alcohols from glycerol without adding hydrogen.

In the present invention, it is described that high yields of 1,2-propanediol and other lower alcohols can be obtained in absence of added hydrogen gas. The process is carried out in an inert atmosphere and can even occur in air.

A preferred class of catalyst is composed of a metal and a microporous carrier. The metal can be deposited on the carrier by impregnation or ion exchange. For impregnation, the desired amount of metal precursor is dissolved in a solvent, usually water. The amount of water is determined as a weight percentage of the catalyst support. It is preferred that the fraction of water is between 0 to about 94 wt % and more preferably between 15 and 94 wt %. While adding the metal precursor solution to the catalyst carrier, the solid is homogenized. After air drying at 60° C., a U-tube containing the catalyst is heated in flowing oxygen, preferably between 300 and 450° C., cooled down to room temperature and subsequently heated in flowing hydrogen up to temperatures ranging preferably between 300 and 450° C.

The metal of the preferred catalyst of the invention is platinum, alloys thereof and mixtures thereof. Using water as solvent, the preferred precursor is platinum tetrammine chloride, $Pt(NH_3)_4Cl_2 \cdot H_2O$.

The preferred weight percentage of platinum, alloys thereof and mixtures thereof deposited on the carrier amounts up to about 6 wt %, preferably from about 0.05 to 4 wt %.

As catalyst carrier, faujasite-type zeolites can be used, preferably a NaY zeolite with framework Si/Al ratio ranging between 2 and 10.

Typically, the reactions are carried out in stainless steel batch reactors of 10 ml connected to a line providing in- and outlet for gasses. Each reactor contains a sample tube and a valve to allow purging or pressurization after sealing. During reaction the reactor content is stirred by means of a magnetic stirrer with a stirring speed ranging from 100 to 600 rpm and more preferably from 200 to 500 rpm.

However, no limitations are placed or implied on whether reactions are carried out continuously or in (fed)-batch-type reactors.

It is generally preferred that the reaction is carried out at a temperature ranging from about 180 to about 300° C., more preferably from about 200 to 260° C.

It is preferred that the concentration of glycerol in water is between 1 and 100 wt %, more preferably between 5 and 50 wt % and most preferably from 10 to 40 wt %.

The optimal reaction time depends on the applied catalyst, the amount of catalyst, the glycerol concentration and the reaction temperature used. With suitable settings of these parameters a substrate conversion can be obtained of at least 90% in concert with a combined selectivity for the lower alcohols of about 70%. 1,2-Propanediol is the preferred alcohol in this invention.

EXAMPLES

The 'conversion' (X) is the amount of glycerol reacted in the conditions described.

The 'selectivity' (S) of a product is defined as the numbers of mole of the product divided by the number of moles of glycerol converted. The 'yield' (Y) is determined as the number of moles of a product divided by the initial number of moles of glycerol present in the reactor.

Example 1

Preparation of a Catalyst According to the Invention 2.7 wt % of Pt supported on zeolite NaY by impregnation occurred as follows. 0.0481 g of $Pt(NH_3)_4Cl_2 \cdot H_2O$ dissolved in 0.8 ml water, was added dropwise to 1.33 g of NaY zeolite, equilibrated in ambient air, while homogenizing. The material was dried overnight in an oven at 60° C. During calcination, the sample is heated to 400° C. at a rate of 5° C./min under an $O_2$-flow of 40 ml/min and held at that temperature for 30 min. The catalyst was cooled to room temperature and subsequently heated at a rate of 5° C./min to 400° C. using 40 ml/min $H_2$-flow and held at that temperature for 1 h.

Example 2

Glycerol Catalytic Conversion According to the Invention

The reaction is carried out in a 10 ml batch reactor with magnetic stirring at 400 rpm. 3 ml of 20 wt % glycerol in water and 4 wt % of the catalyst described in example 1, was added to the reactor. The reactor was then purged with nitrogen gas. After heating to a reaction temperature of 230° C., the reactor was kept at this temperature for 17 h. After cooling to about 15° C., samples of the liquid phase were taken. The samples are analyzed using gas chromatography on a PORAPLOT Q column (50 m×0.32 mm, $d_f$=10 µm). The initial temperature of 230° C. is kept for 8 minutes. Then the column is heated at 5° C./min to 250° C. and remains at that temperature for 30 minutes. The column outlet was then passed over a methanator and a FID detector. At a conversion of 90% the combined selectivity for lower alcohols is 78%. The yield of the main product, 1,2-propanediol, is 53% with a selectivity of 59%. Ethanol is produced as a side-product with 13% selectivity. The combined selectivities for methanol, n-propanol and ethylene glycol are 8%.

Example 3

A reaction is carried out as described in example 2, the applied catalyst being prepared according to the procedure of example 1, using an impregnation volume of metal salt of 0.2 ml instead of 0.8 ml. At a conversion of 95%, the combined selectivity for all lower alcohols is 70%, including a 1,2-propanediol yield of 45%

Example 4

The reaction is carried out as in example 2, using a catalyst prepared according to the procedure of example 1. The impregnation volume is 1.25 ml instead of 0.8 ml. At a conversion of 89%, a combined selectivity for alcohols of 86% and a 1,2-propanediol yield of 53% is obtained.

Example 5

The catalyst used in this example is regenerated from the experiment in example 2. Regeneration implies centrifugation or filtration without further treatment. At a conversion of 93% the combined selectivity for lower alcohols is 72%. The yield of the main product, 1,2-propanediol, is 46% with a selectivity of 49%. Ethanol is produced as a side-product with 14% selectivity.

Example 6

The reaction is carried out as in example 2, using 0.03 g of a commercial 5 wt % Pt on carbon in combination with 0.17 g of a air equilibrated commercial NaY (Si/Al=2.7) zeolite as catalysts. At a conversion of 74%, a combined selectivity for alcohols of 76% and a 1,2-propanediol yield of 44% is obtained.

Comparative Example 1

A reaction is carried out as in example 2, using a hydrogen gas pressure of 10 bar. A conversion of 41% and a 1,2-propanediol yield of 24% is obtained.

Comparative Example 2

The reaction is carried out as in example 2, using the catalyst of example 1, activated and reduced at 550° C. instead of 400° C. A conversion of 31% is obtained with a 1,2-propanediol yield of 9%.

Comparative Example 3

The reaction is carried out as in example 2. The applied catalyst is a commercial 5 wt % Pt on carbon. The reaction is carried out with the same amount of Pt in the reactor. A conversion of 58% is obtained with 1,2-propanediol yield of 22%.

Comparative Example 4

The reaction is carried out as in example 2. The applied catalyst is a 2.7 wt % Pt impregnated on gamma-alumina according to the state of the art technique. Pretreatment of the catalyst is carried out as described in example 1. A glycerol conversion of 99.6% is obtained with a reaction yield of 16% 1,2-propaandiol.

Comparative Example 5

The reaction is carried out as in example 2. The applied catalyst is 2.7 wt % Pt impregnated on HY according to the procedure described in example 1. Pretreatment of the catalyst is carried out as described in example 1. A glycerol conversion of 66% is obtained with a reaction yield of 8% 1,2-propaandiol.

The invention claimed is:
1. A catalytic process for the production of lower alcohols from glycerol, wherein the lower alcohol is selected from the group consisting of ethanol, n-propanol, methanol, ethylene glycol and 1,2-propanediol and that the process of glycerol conversion is a single-step catalytic process which is without addition of hydrogen or does not require addition of hydrogen comprising subjecting a water and glycerol reaction mixture to heating in the presence of an heterogeneous catalyst comprising a metal on a microporous carrier and to set reaction mixture in amounts sufficient to induce or to control catalytic hydrogenation.
2. The catalytic process of claim 1, wherein said microporous carrier is an acid microporous carrier.
3. The catalytic process according to claim 1, wherein the microporous carrier is a zeolite.
4. The catalytic process according to claim 1, wherein said metal is selected from the Group VIII metals, alloys thereof and mixtures thereof, and wherein said microporous carrier is a faujasite-type zeolite carrier.
5. The catalytic process according to claim 4, wherein said metal is a supported metal.
6. The catalytic process according to claim 5, wherein said supported metal is on a carbon support.
7. The catalytic process according to claim 5, wherein the supported metal is prepared by ion exchange or impregnation.
8. The catalytic process according to claim 7, wherein the amount of aqueous salt solution used for impregnation is from 0.01 to 94 wt % of the catalyst support, more preferably from 15 to 94 wt %.
9. The catalytic process according to claim 1, wherein the initial concentration of glycerol is from 1 to 100 wt %.
10. The catalytic process according to claim 1, wherein the initial concentration of glycerol is from 5 to 50 wt % and preferably from 10 to 40 wt %.
11. The catalytic process according to claim 5, wherein the supported metal is prepared by using an amine complex salt which is then decomposed.
12. The catalytic process according to claim 5, wherein the supported metal is platinum or alloys thereof or mixtures thereof.
13. The catalytic process according to claim 12, wherein the alloys or mixtures of platinum may comprise a metal selected from the groups consisting of Pd, Rh, Ru, Cu, Cr, Sn, and Ni.
14. The catalytic process according to claim 1, wherein the carrier is loaded with metal up to 6 wt %.
15. The catalytic process according to claim 1, wherein the carrier is loaded with metal between 0.05 to 4 wt %.
16. The catalytic process according to claim 3, wherein the zeolite support is an alkali form of Y-zeolite including NaY, KY, RbY and CsY, and NaY with 2<Si/Al<5.
17. The catalytic process according to claim 1, wherein a glycerol conversion of 90% or higher is obtained, with a combined selectivity of lower alcohols of 70% or higher.
18. The catalytic process according to claim 1, wherein a glycerol conversion of 90% or higher is obtained, a combined selectivity of lower alcohols of 70% or higher of which at least 50 mol % is 1,2-propanediol.
19. The catalytic process according to claim 1, wherein the temperature is from 180 to 300° C.
20. The catalytic process according to claim 1, wherein the temperature is from 200 to 250° C.
21. A process for the selective production of lower alcohols from glycerol, said process comprising a single step in which an acid heterogeneous catalyst is used without addition of hydrogen or with addition of a gas that contains less than 2 parts per million of hydrogen, wherein said acid heterogeneous catalyst comprises a molecular sieve and a metal selected from the Group VIII metals, alloys thereof and mixtures thereof.

* * * * *

UNITED STATES PATENT AND TRADEMARK OFFICE
CERTIFICATE OF CORRECTION

| | | |
|---|---|---|
| PATENT NO. | : 8,080,692 B2 | Page 1 of 1 |
| APPLICATION NO. | : 12/520941 | |
| DATED | : December 20, 2011 | |
| INVENTOR(S) | : D'hondt et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 302 days.

Signed and Sealed this
Twenty-ninth Day of May, 2012

David J. Kappos
*Director of the United States Patent and Trademark Office*